United States Patent [19]

McCandless et al.

[11] Patent Number: 5,461,232
[45] Date of Patent: Oct. 24, 1995

[54] PULSE TRANSMISSION SCINTIGRAPHIC IMAGING

[76] Inventors: Brian K. McCandless, 57 Patroon Pl., Loudonville, N.Y. 12211; Jeffrey A. Cooper, 140 Brandon Ter., Albany, N.Y. 12203

[21] Appl. No.: 1,824

[22] Filed: Jan. 8, 1993

[51] Int. Cl.[6] .................................................. G01T 1/166
[52] U.S. Cl. ................................. 250/363.04; 250/498.1
[58] Field of Search ............................... 375/4, 120, 160; 250/363.04, 498.1, 496.1; 364/413.24

[56] References Cited

U.S. PATENT DOCUMENTS

| | | | |
|---|---|---|---|
| 5,155,365 | 10/1992 | Cann et al. | 250/363.02 |
| 5,165,410 | 11/1992 | Warne et al. | 128/653 R |
| 5,289,008 | 2/1994 | Jaszczah et al. | 250/363.03 |
| 5,376,795 | 12/1994 | Hasagawa et al. | 250/363.04 |
| 5,391,877 | 2/1995 | Marks | 250/363.04 |

OTHER PUBLICATIONS

Feldcam et al., "Practical Cone–Beam Algorithm", J. Opt. Soc. Am., 1984, 1, 612–619.

Gullberg et al., "Review of Convergent Beam Tomography in Singe Photon Emission Computed Tomography", Phys. Med. Biol. 1992, 37, 507–534.

Moore, Attenuation Compensation, *Computed Emission Tomography*, Oxford University Press, 1982, 339–350.

Bailey et al., "Improved Spect Using Simultaneous Emission and Transmission Tomography", J. Nucl. Med. 1987, 28, 844–851.

*Primary Examiner*—David P. Porta
*Assistant Examiner*—David Vernon Bruce
*Attorney, Agent, or Firm*—Schmeiser, Olsen & Watts

[57] ABSTRACT

A pulse transmission scintigraphic imaging system for providing image data for attenuation correction and fiducial alignment. The system includes a shuttered photon flood transmission source, secured opposite an Anger gamma scintillation camera by an adjustable armature, a motorized photon-occluding shutter mechanism for producing photon pulses from the photons emitted by the flood source and a gating system for providing a signal to the gamma camera indicative of the presence of a photon pulse (shutter mechanism open) or the absence of a photon pulse (shutter mechanism closed).

16 Claims, 6 Drawing Sheets

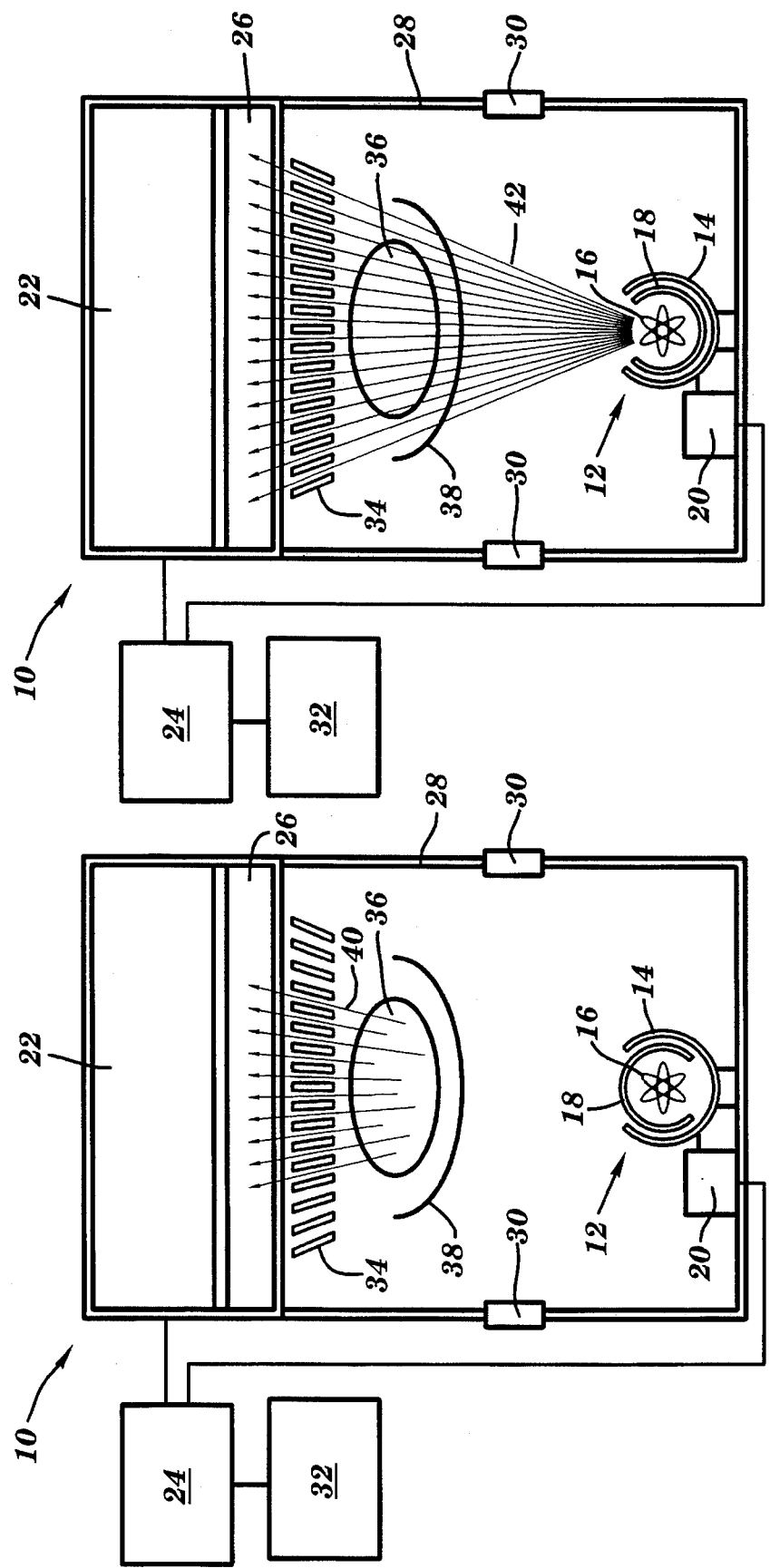

PULSE TRANSMISSION SCINTIGRAPHIC IMAGING

FIELD OF THE INVENTION

The present invention relates to a nuclear medical imaging system and, more particularly, to a medical imaging system which utilizes a shuttered transmission source in conjunction with an Anger gamma scintillation camera to provide image data for attenuation correction and fiducial alignment.

BACKGROUND OF THE INVENTION

The field of Nuclear Medicine has utilized radionuclides to produce images to assist in the diagnosis of disease for more than three decades. Commonly, an Anger gamma scintillation camera is utilized to develop an image corresponding to the radionuclide distribution within a patient. The gamma camera generally includes a sodium iodide (NaI) scintillation crystal to detect and convert the photons emitted by a radionuclide within the patient into light pulses, a collimator, interposed between the scintillation crystal and the patient, to permit detection only of photons with the desired orientation, an array of photomultiplier tubes to convert the light pulses produced by the scintillation crystal into electrical signals, a pulse height analyzer to isolate the photopeak corresponding to the isotope within the patient by discarding the electrical signals created by scattered, background and/or other spurious radiation, output devices, such as a cathode ray tube or the like, to provide visual and hard copy images of the output of the pulse height analyzer and a computer for controlling the overall operation of the gamma camera and for analyzing the collected data. Using the Anger camera, gamma rays emitted from the isotopes in the patient's body can be localized in a two dimensional projection and formatted onto standard radiographic film.

Over the last decade, three dimensional image construction using single photon emission computed tomography (SPECT) has become widely used in the field of Nuclear Medicine as a method to enhance spatial and contrast resolution. SPECT uses multiple different projections (usually acquired in a 180 or 360 degree arc around the patient) to allow a computer to reconstruct the three dimensional image of isotope distribution. This information can be viewed using a number of different methods such as tomographic slices along a chosen axis (transaxial, coronal, sagittal, etc.), surface or volume rendering, polar maps or the like.

Unfortunately, as currently practiced, SPECT imaging of radioisotope studies in the human body suffers from several disadvantages. For example, photons emitted from radioisotopes in the organ of interest are attenuated by the body tissue that lies between the organ of interest and the detector-camera. This photon-attenuation varies with each different projection and results in image distortion and artifact.

Another difficulty physicians face when attempting to interpret nuclear medicine images is the lack of anatomic detail in many of the images. Nuclear medicine frequently involves functional imaging in which a physiologic process rather than an anatomical structure is being examined. Common physiologic processes that are investigated include tissue viability, perfusion, bone metabolism, leukocyte distribution and monoclonal antibody binding. Unfortunately, areas of increased radionuclide activity on the scintigraphic images provided by a gamma scintillation camera often indicate the presence of the physiologic process of interest without clear indication of its precise anatomic location.

SUMMARY OF THE INVENTION

In order to avoid the disadvantages of the prior art, the pulse transmission system of the present invention utilizes a shuttered transmission source, which may be attached to a standard Anger gamma scintillation camera by an adjustable armature, to provide data for fiducial alignment and data for correcting the attenuation that occurs in each pixel of an acquired image. In particular, the shuttered transmission source includes a photon flood source which is positioned on the opposite side of a patient from the gamma camera, a motorized photon-occluding shutter mechanism for producing intermittent photon pulses from the photons emitted by the photon flood source and a gating system for providing a signal to the gamma camera that indicates the presence of a photon pulse (shutter mechanism open) or the absence of a photon pulse (shutter mechanism closed). The gamma camera will have a collimator attached thereto, interposed between the scintillation crystal and the patient, to permit detection of photons with the desired alignment.

The present invention is designed to use a radionuclide in its flood source that is identical to the radionuclide which has been administered to the patient being imaged. A radionuclide can be used in the flood source that is different from the radionuclide in the patient but this will complicate the calculation of the attenuation coefficients. In operation, the patient to be imaged has a radiopharmaceutical administered in the usual manner. Subsequently, the patient is positioned in front of the gamma camera, between the gamma camera and the flood source, and image data is acquired with both the flood source shuttered (emission image) and unshuttered (transmission image). The administered radionuclide is detected by the gamma camera as photons are emitted from the patient while the flood source is shuttered. Without moving the patient or camera, the shutter mechanism is opened and both the photons emitted from the patient and the photons emitted from the flood source (some of which pass through the patient as a transmission image and some of which pass along side the patient) are detected by the gamma camera. Unobstructed (without the patient) image data corresponding to the photons emitted by the flood source may also be acquired by the gamma camera.

During planar imaging, this process is performed in a single gamma camera position. During tomographic imaging using the traditional stop-and-shoot format, the process is repeated throughout the imaging process with image data being acquired with the shutter mechanism open and with the shutter mechanism closed while the camera is in the same position. In particular, multiple image sets are acquired in both a shuttered and unshuttered mode to gain emission and transmission data at different camera angles around a patient.

In the present invention, the acquired image data is processed for three primary purposes: 1. Standard emission images; planar or tomographic images (SPECT) can be reconstructed from the images acquired while the flood source is shuttered. 2. Transmission images for fiducial alignment; image data acquired while the shutter is open can be used to produce transmission images (the flood source can be filled with enough radionuclide so that the vast majority of the photons detected by the camera are transmission photons or the emission counts in each pixel can be subtracted from the transmission data). 3. Attenuation correction images; using transmission image data and the unobstructed (without the patient) flood data, the attenuation coefficient can be calculated for each pixel in each camera projection. Using these attenuation coefficients, emission images can be corrected for attenuation.

The flood source is a small water-tight plexiglass compartment which contains a supply of a radionuclide, typically 1 to 20 milliliters (ml) in volume depending upon the application. The contents of the flood source compartment must be changeable to allow for the use of different radionuclides or the replenishing of the radionuclide therein when physical decay of the isotope mandates this. The flood source is supported by an adjustable armature which allows it to be positioned at or near the focal point, focal line or focal plane of the collimator. There is a clear space between the flood source and the gamma camera so as not to obstruct photons traveling from the flood source to the camera.

Optimally, the flood source is filled with enough isotope to produce 50 to 100 thousand counts per second when the shutter mechanism is open. This results in a number of advantages. First, with a high photon flux coming from the flood source, there is a better resolution in the transmission image as well as statistically more accurate data for the calculation of attenuation coefficients. Second, the high photon flux provided by the flood source reduces the time interval required with the shutter mechanism open, thereby reducing the total imaging time. Finally, with a high photon flux from the flood source, the images acquired when the shutter mechanism is open become less of a mixture of emission and transmission data and approach pure transmission images, thereby lessening the need to correct the transmission data.

Many different isotopes may be used in the present invention including gallium-67, indium-111, iodine-131, iodine-123, thallium-201, or technetium-99$^m$. For example, thallium-201 may be utilized for myocardial perfusion imaging. As is well known in the art, imaging of the myocardium is plagued by variable attenuation of the surrounding tissue. The human chest contains highly attenuating material such as the sternum, less attenuating material such as the mediastinum and muscles, and low attenuation material such as the air in the lungs. This results in regional reductions of the observed radionuclide in the myocardium which can be confused with regions of decreased blood flow. Using 0.5 mCi of thallium-201 in the flood source and the usual dose of 3 mCi thallium-201 administered intravenously to the patient, the present invention can compensate for the above-described phenomenon by removing these attenuation artifacts.

The shutter mechanism is designed to interpose a photon-occluding shield between the flood source and the gamma camera at intervals. In particular, the photon-occluding shield is adapted to be intermittently interposed between the flood source and gamma camera (shutter closed) and withdrawn (shutter open), thereby producing pulses of flood source photons. The photon-occluding shield is constructed of a highly photon-attenuating medium such as lead or the like which acts to stop the photons. When the shutter shield is open, flood source photons impinge upon the gamma camera. When the shutter shield is closed, however, the photons are prevented from doing so. Preferably, the shutter shield is operated automatically with a small motor or the like under the control of the gamma camera computer, although the shutter shield may be operated independently of the gamma camera computer or under manual control.

The gating system is adapted to signal the gamma camera and its associated computer as to when the shutter shield is open and when it is closed. In particular, electrical switches, electrical contacts, a photon cell or a variety of other devices may be used to sense the position of the shutter shield relative to the flood source.

The present invention may be utilized with gamma cameras fitted with various types of converging collimators such as cone-beam, fan-beam and astigmatic collimators. In addition, the principle of using a pulse of transmission photons from a shuttered flood source could be applied to standard parallel hole collimators but there are several advantages to using converging collimators. For example, converging collimators allow the use of an exponentially smaller amount of radionuclide in the flood source. By positioning the radionuclide flood source at the focal point or line of the collimator, the gamma camera's efficiency in detecting photons is extremely high. The use of less radionuclide results in lower cost, less radionuclide waste and lower radiation exposure to the patient from the transmission source.

The second advantage of converging collimators is mechanical in nature. In particular, converging collimators allow a very small flood source to be constructed (a point or a line) instead of the "sheet" source required in parallel hole collimation. Unlike the large sheet source, the point or line sources are light, easy to support from the housing of the gamma camera and easy to shield.

The third advantage particular to the converging cone beam collimator is that it dramatically reduces the scattered photons in the transmission and flood images. In particular, collimation only permits the camera detection of photons arriving at the camera via a direct route from the radionuclide. Scatter, which can constitute twenty to thirty percent of the counts in an image, occurs when photons that normally would not be detected by the camera are deflected from their initial course and are subsequently detected by the camera. As a result, the position of the radionuclide in the body is erroneously assigned. However, in transmission images derived from a point flood source using a cone-beam collimator, the geometry of the device precludes this error; scattered photons coming from the focal point will not pass through the collimator. Only by undergoing two or more precisely angled deflections will scattered photons be accepted, and this does not occur with significant frequency.

Finally, a fourth advantage is the benefit intrinsic to the general use of converging collimators. Converging collimators offer improved spatial resolution by focusing more of the gamma camera on the object of interest.

The image data provided by the gamma camera can be processed for several purposes by the gamma camera computer: conventional emission imaging; transmission imaging for anatomic information and fiducial alignment; and attenuation corrected emission imaging for more quantitatively accurate information.

Emission data can be used as a simple planar image or reconstructed with standard SPECT techniques. SPECT reconstruction can be performed using commonly available filtered backprojection methods.

Transmission data can be used to construct images for fiducial alignment either as planar images or SPECT. With planar imaging, the unprocessed transmission image can be used to gain qualitative information about regional anatomy. However, this transmission image will also contain information that was derived from the photons being emitted by the radionuclide within the patient. The unprocessed transmission image can be corrected for this by subtracting the counts/second in each pixel in the emission image from the transmission image. This corrected transmission image can also be used to qualitatively assess regional anatomy. Comparison of the corrected with the uncorrected transmission images as well as with the emission images can help the diagnostician identify the location of photon emissions.

A two dimensional representation (image) of the line integral of the attenuation coefficient for each pixel can also be derived from the transmission and flood image data using the following formula:

$$\ln\left(\frac{C_o}{C_x}\right) = \sum_i \mu_i x \quad (1)$$

where $C_o$ is the count rate in a corrected flood image, $C_x$ is the count rate in the transmission image and $\Sigma_i \mu_i x$ is the line integral of attenuation coefficients $\mu$ along a path x from the source, through the attenuating material to the detector. The line integral of attenuation coefficients is a value which is assigned to each pixel and can be viewed as a planar image. A plurality of planar images can also then be reconstructed using standard filtered backprojection into SPECT images.

The corrected flood image $C_o$ is the counts/pixel/second detected by the gamma camera when the shutter is open subtracted by the counts/pixel/second when the shutter is closed. These flood images are acquired without the patient and are not affected by the positioning of the camera. Consequently, the corrected flood image can be used in calculating the attenuation in all of the imaging performed in a particular study. Correction of the flood image for physical decay of the isotope during the study is usually not necessary if the study is completed in a period of time which is short relative to the physical half life of the isotope.

Attenuation corrected emission images can be generated using both planar and SPECT techniques. In planar imaging, the attenuation coefficient derived in the above equation for each pixel is multiplied by the counts in each corresponding pixel of the emission image.

In SPECT imaging, the attenuation coefficients are calculated for each voxel by backprojection of the line integral of the attenuation coefficients derived from the flood images and the transmission images. The attenuation correction factor of each voxel is derived from the attenuation coefficients using the equation:

$$C(x,y,z) = \left[\frac{1}{P} \sum_{i=1}^{P} \exp(-\mu l(x,y,z,\theta_i))\right]^{-1} \quad (2)$$

where C is the correction factor for the voxel (x,y,z), P is the projection number, $\theta$ is the angle of projection and $l(x,y,z,\theta)$ is the distance from the voxel (x,y,z) to the boundary of the attenuating material along the projection P at angle $\theta$. In particular, the correction factor C for the voxel (x,y,z) is equal to the inverse of the average of the attenuation coefficients for P projections over 360 degrees around the voxel. Attenuation corrected images may be obtained by multiplying the count density of each voxel in the emission image by the corresponding correction factor for that voxel. The correction factor defined by equation 2 for each voxel (x,y,z) is appropriate when using a cone-beam collimator. If a fan-beam or parallel hole collimator is utilized, the correction factor may be calculated for each voxel (x,y) by deleting the "z" coordinate in equation 2. Other methods for attenuation correction are usable once an attenuation coefficient map is derived from equation 1.

The present invention provides fiducial alignment of images acquired with planar emission scintigraphy and emission tomographic scintigraphy (SPECT). Unfortunately, as well known in the art, emission images often show radionuclide uptake at sites in the body without clear anatomic reference to indicate the specific organ or tissue in which the activity is occurring. Transmission images acquired with the present invention are produced with higher photon flux and provide an image of surrounding structures, not just the organs exhibiting radionuclide uptake. This provides an image with better anatomical detail and an anatomic reference to relate the physiologic emission image to. Advantageously, this transmission image can be superimposed on the emission image because the patient was not repositioned during the data acquisitions.

A second major benefit of the present invention is the attenuation correction of emission images. Again, as well known in the art, attenuation of emission photons results in image distortion and artifact. The image distortion and artifact that results from attenuation within the body can be corrected with the present invention in the manner disclosed above. The resulting image information is more reliable and contains more accurate quantitation of the localization of the radionuclide.

The present invention utilizes the same isotope for the calculation of the attenuation coefficient and for emission imaging. In addition, attenuation information and emission data are obtained virtually simultaneously without moving the patient. Other currently available attenuation correction methods require a separate imaging session at a later time, thereby allowing the radionuclide in the patient to decay and/or be excreted, potentially resulting in attenuation coefficient error. Other attenuation correction methods utilize a simultaneous process which relies on two different isotopes. This may result in an error in the calculated attenuation coefficient since attenuation is a function of the photon energy. In particular, the simultaneous use of two different isotopes results in the down-scatter of photons from the higher energy isotope into the energy-window of the lower energy isotope.

BRIEF DESCRIPTION OF THE DRAWINGS

FIGS. 1–2 are end views of a pulse transmission scintigraphic imaging system according to the preferred embodiment of the present invention;

DETAILED DESCRIPTION OF THE INVENTION

Figure 4:
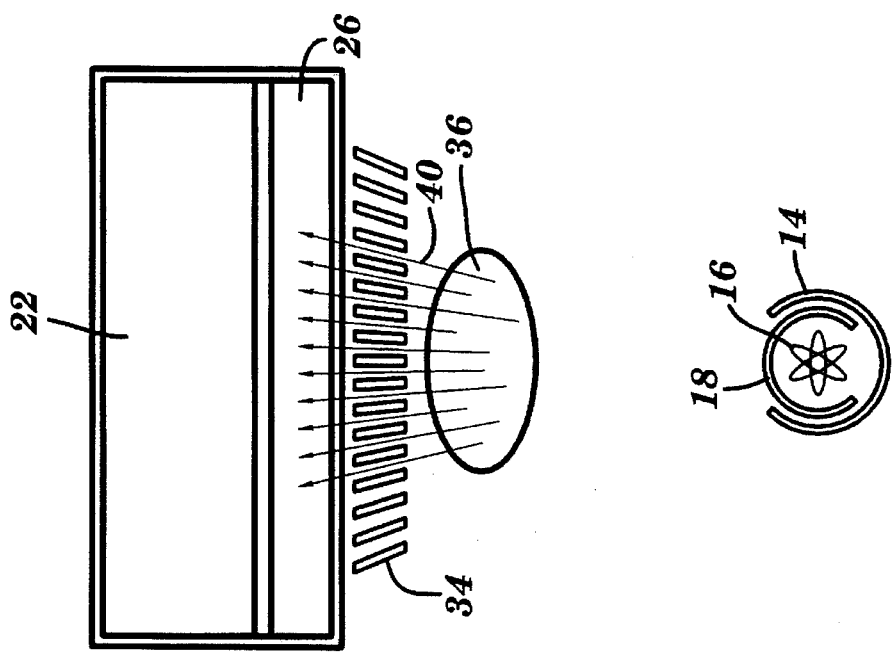
FIGS. 3–6 are partial end views of a single-head camera tomographic imaging system including a shuttered transmission source.

Referring now specifically to the drawings, there is illustrated a pulse transmission scintigraphic imaging system according to the preferred embodiment of the invention, generally designated as 10, wherein like reference numerals refer to like parts throughout the drawings.

As illustrated in FIGS. 1–2, the pulse transmission system of the present invention includes a shuttered transmission source, generally designated as 12, having a flood source compartment 14 containing a supply of a radionuclide photon flood source 16, a motorized photon-occluding shutter mechanism 18 for producing intermittent photon pulses using the photons emitted by the photon flood source 16, and a gating system 20 for providing a signal to a standard Anger gamma scintillation camera 22 and associated gamma camera computer 24 relative to the presence of a photon pulse (shutter mechanism 18 open) or the absence of a photon pulse (shutter mechanism 18 closed). The shuttered transmission source 12 is adjustably attached opposite the scintillation crystal 26 of the gamma camera 22 by an armature 28 having length adjustment members 30. An output system 32 for providing visual and/or hard copy images of the image detected by the gamma camera 22 is operatively connected to the gamma camera computer 24. A collimator 34 may be attached to the gamma camera 22 to reduce the detection of scattered photons.

FIGS. 1–2 also illustrate the planar (single gamma camera position) imaging of a patient 36 who is supported by a patient support member 38 between the gamma camera 22 and the shuttered transmission source 12. In FIG. 1, a plurality of emitted photons 40, corresponding to a radionuclide which has been previously administered to the patient 36, are detected by the gamma camera 22 after passing through the collimator 34 and impinging upon the scintillation crystal 26, thereby providing a standard emission image. As illustrated, the photon flood source 16 is shuttered by the photon-occluding shutter mechanism 18 during the acquisition of the emission image. Similarly, as illustrated in FIG. 2, a transmission image is acquired by unshuttering the photon flood source 16 without moving the patient 36 or gamma camera 22, wherein a plurality of the photons 42 emanating from the photon flood source 16 (which contains the same radionuclide that has been administered to the patient) pass through the patient 36 and collimator 34 and are subsequently detected by the gamma camera 22. The transmission image, which also contains photon information corresponding to the photons 40 emitted by the patient, may be corrected by the gamma camera computer 24 by subtracting the counts/second in each pixel in the emission image from the transmission image. Typically, the photons 40 emitted by the patient are less abundant than the photons 42 emitted by the flood source 16 and account for less than five percent of the total counts detected by the gamma camera 22.

Figure 3:
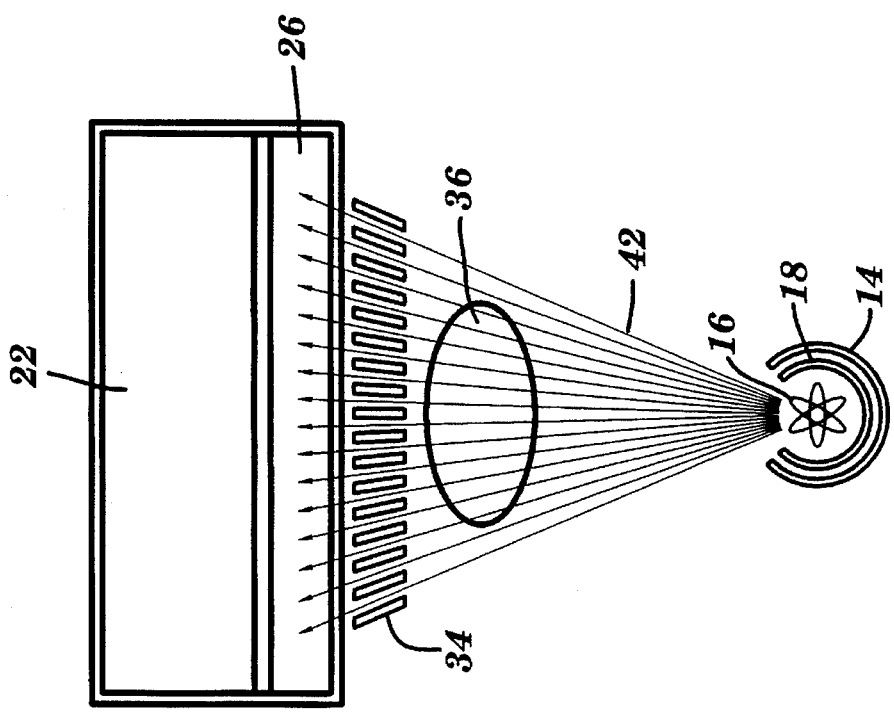
Figure 6:
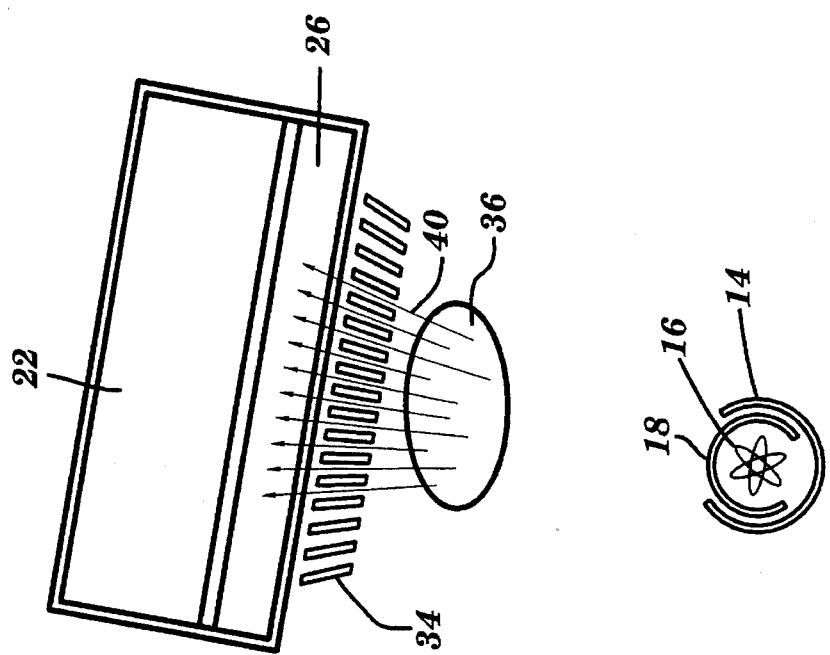
Figure 5:
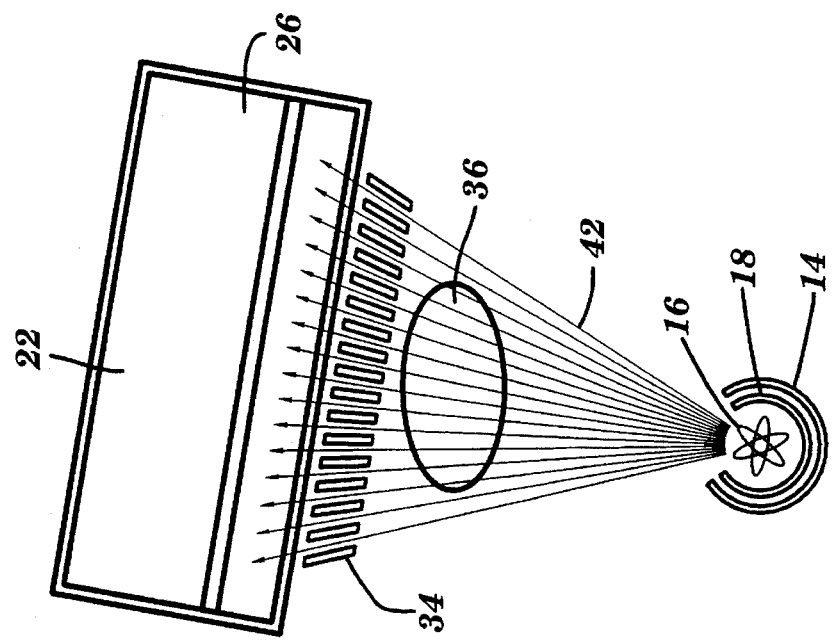

A single-head camera tomographic imaging system for acquiring transmission and emission images at a plurality of projection angles and including a pulse transmission system in accordance with the present invention is illustrated in detail in FIGS. 3–6. For sake of clarity, only those components of the present invention which are required for an understanding of the tomographic imaging process have been illustrated. During tomographic imaging using the standard stop-and-shoot format, wherein the gamma camera 22 and shuttered transmission source 12 are supported by a gantry (not shown) which is adapted to be rotated about a patient 36, multiple transmission and emission image sets are acquired in both a shuttered and unshuttered mode. FIG. 3 illustrates the acquisition of a transmission image for a first projection $P_1$ at a projection angle of $\theta_1$. In particular, a plurality of photons 42, emitted by the unshuttered flood source 16, pass through the patient 36 and collimator 34 and are detected by the gamma camera 22. As shown in FIG. 3, a corresponding standard emission image for the first projection $P_1(\theta_1)$ is acquired without moving the patient 36 and the camera 22, by detecting the photons 40 emitted by the patient 36 while the photon flood source 16 is being shuttered by the photon-occluding shutter mechanism 18. As illustrated in FIGS. 5–6, second transmission and emission images, respectively, are obtained for a second projection $P_2$ at a projection angle of $\theta_2$ ($\theta_1 \neq \theta_2$). This process is repeated for a number of additional projections as the gantry is periodically rotated a predetermined distance along an arc (typically 180 or 360 degrees) about the patient 36. A three dimensional image of the isotope distribution in the patient 36 can be reconstructed by the computer 24 using standard SPECT reconstruction techniques.

Figure 8:
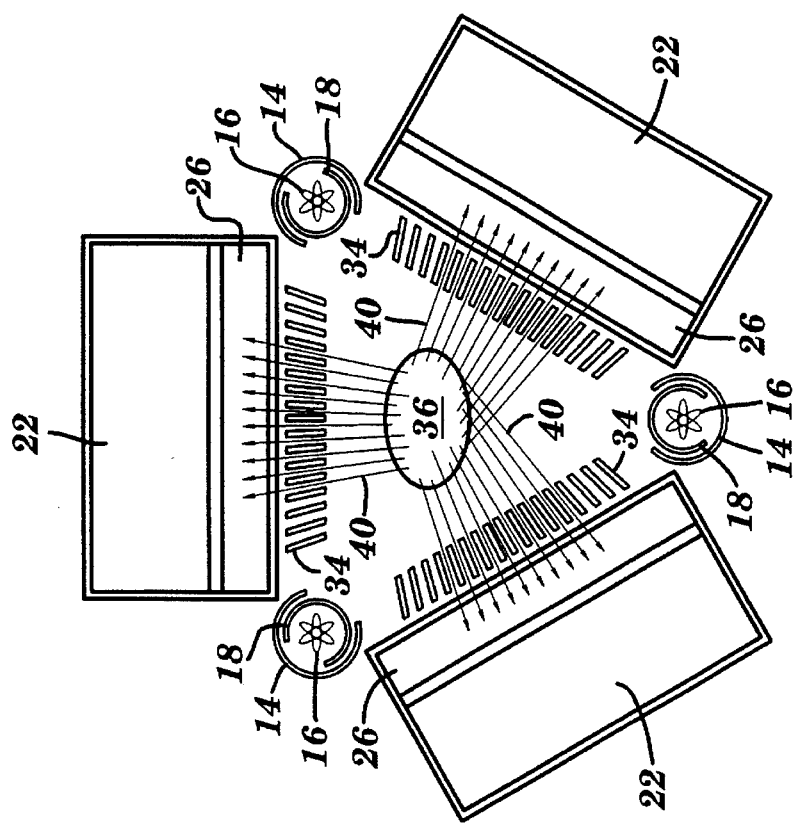
FIGS. 7–10 are partial end views of a triple-head camera tomographic imaging system including a shuttered transmission source.
Figure 7:
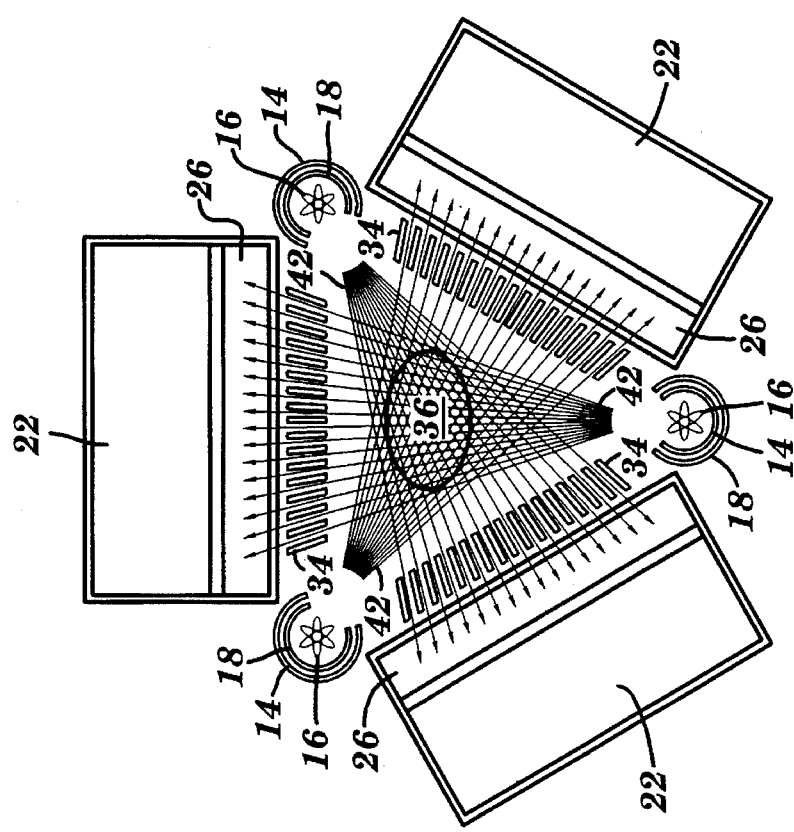
Figure 10:
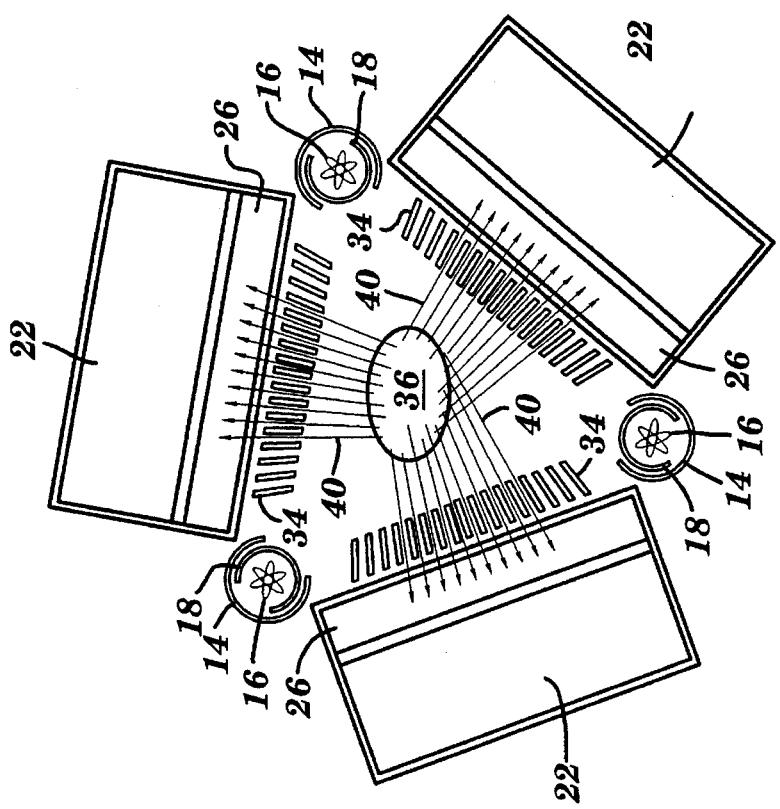
Figure 9:
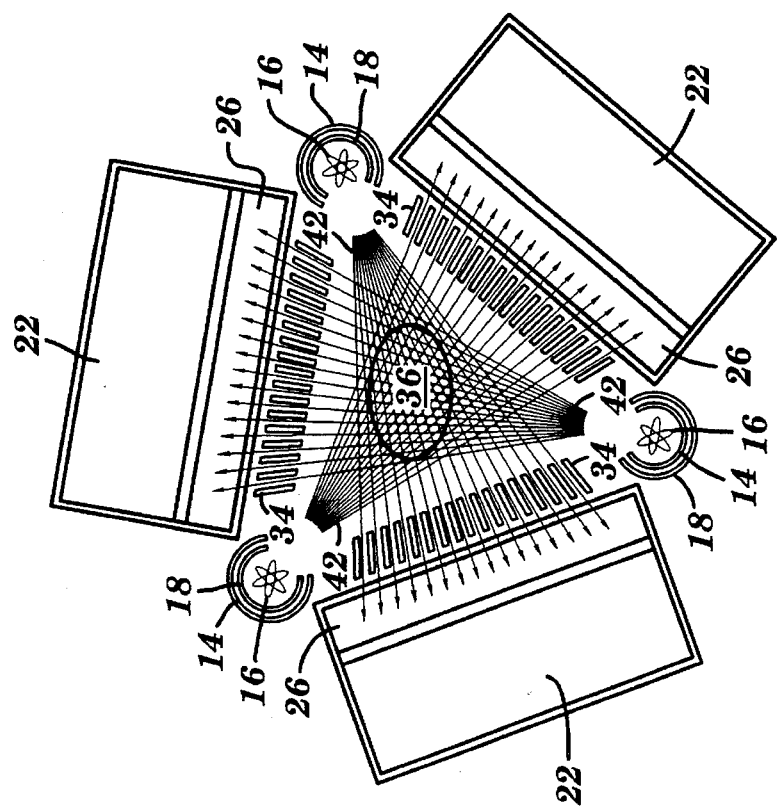

A triple-head tomographic imaging system incorporating the pulse transmission system of the present invention is illustrated in FIGS. 7–10. As the name implies, three sets of gamma cameras 22 and their associated shuttered transmission sources 12 are symmetrically supported about a patient 36 by a rotatable gantry (not shown). FIGS. 7–8 illustrate the acquisition of transmission and emission images, respectively, for a first projection $P_1$ taken at a projection angle of $\theta_1$. Similarly, FIGS. 9–10 illustrate the acquisition of transmission and emission images, respectively, for a second projection $P_2$ taken at a projection angle of $\theta_2$, subsequent to a predetermined rotation of the gantry about the patient 36. Again, a three dimensional image of the isotope distribution in the patient 36 can be reconstructed by the computer 24 using standard SPECT reconstruction techniques, based upon the plurality of emission images acquired as the gantry is rotated about the patient.

During planar and tomographic (SPECT) imaging, transmission images (uncorrected or corrected) can be used to gain information for anatomic reference and fiducial alignment when correlated with a corresponding emission image. In particular, a transmission image may be superimposed on a corresponding emission image under control of the gamma camera computer 24, wherein a single composite image is produced by the output system 32 for display on a cathode ray tube or the like or as a hard copy image formatted onto standard radiographic film. Alternatively, hard copy transmission and emission images may be manually superimposed on each other, thereby producing a composite image.

Figure 12:
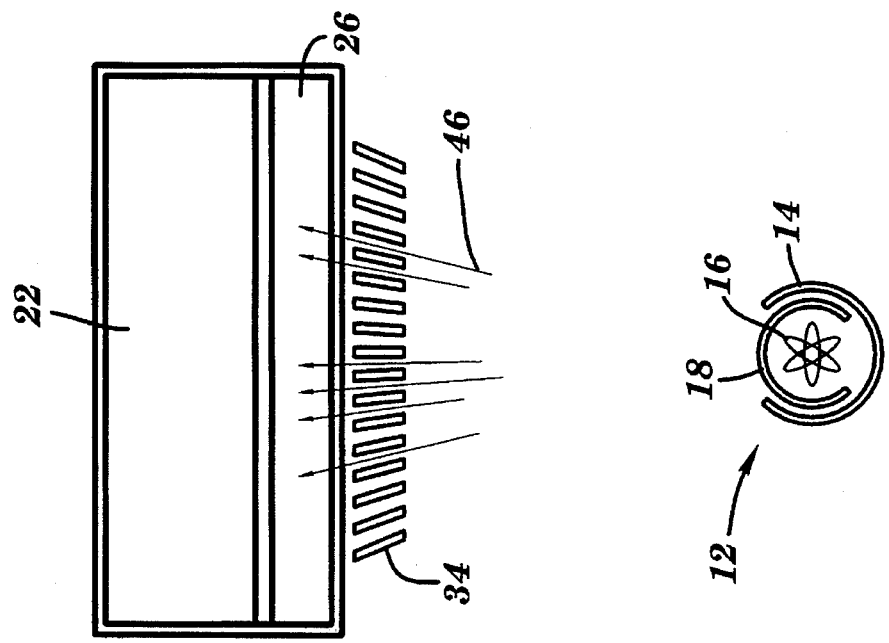
FIGS. 11–12 illustrate a system for obtaining a corrected flood image $C_o$.
Figure 11:
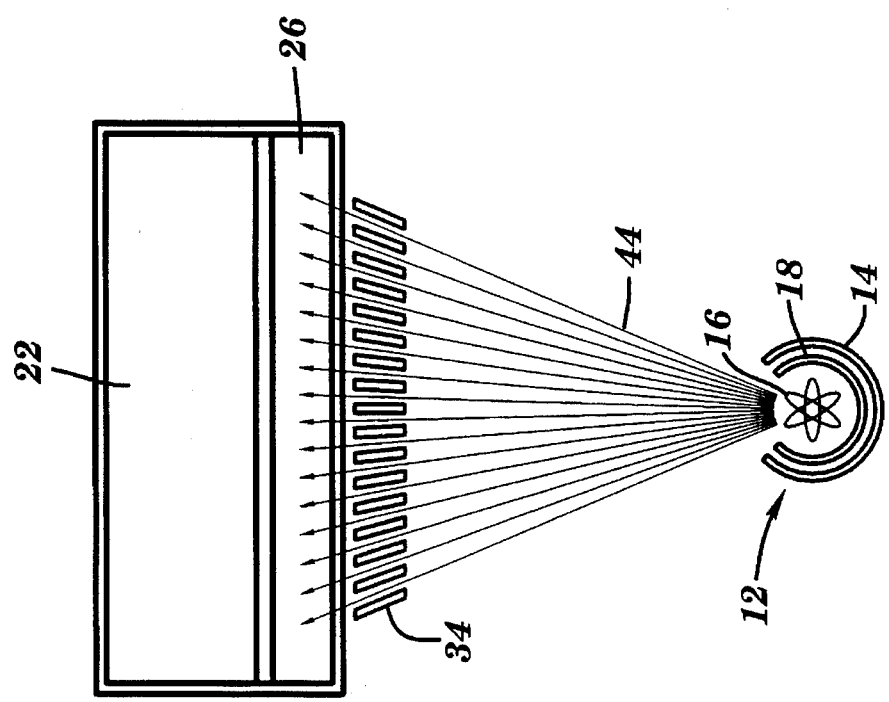

Attenuation corrected planar emission images may be generated, under the control of the gamma camera computer 24, by multiplying the counts within each pixel of the emission image by a corresponding attenuation correction factor that has been calculated in accordance with equation (1) above. Prior to the calculation of the attenuation coefficients, a corrected flood image $C_o$ (obtained without the patient) equal to the counts/pixel/second detected by the gamma camera 22 when the flood source 16 is unshuttered subtracted by the counts/pixel/second when the flood source 16 is shuttered, must be acquired. FIGS. 11–12 illustrate the pulse transmission system of the present invention during the acquisition of the photon data required for the determination of the corrected flood image $C_o$. As illustrated, the flood source photons 44 and 46 emitted while the flood source 16 is unshuttered and shuttered, respectively, are detected by the gamma camera 22.

Analogously, attenuation corrected tomographic (SPECT) emission images may be obtained, under the control of the gamma camera computer 24, by multiplying the count density of each voxel in the emission image by the corresponding correction factor for that voxel, wherein the correction factors are determined in accordance with equations (1) and (2) above.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

We claim:

1. In a nuclear medical imaging system, a pulse transmission system comprising:

means for detecting photons and for producing image data corresponding thereto;

flood source means for providing a supply of photons, said flood source means including means for storing a predetermined quantity of a radionuclide and means for intermittently producing pulses of photons, said pulses of photons being emitted by the radionuclide within said storing means; and armature means for positioning said flood source means substantially opposite said photon detecting means, wherein said photon detecting means is adapted to detect the photons produced by said photon pulse producing means; and means for positioning a patient between said photon pulse producing means and said photon detecting means, wherein said patient has been administered a radionuclide;

wherein said means for detecting photons and for producing image data corresponding thereto further includes: means for obtaining emission image data corresponding to the photons emitted by the radionuclide within said patient while said photon pulse producing means is not producing the pulses of photons; means for obtaining transmission image data corresponding to at least said pulse of photons, said pulse of photons being emitted by the radionuclide within said a storing means; and means for producing image data for fiducial alignment from at least said transmission image data.

2. The system according to claim 1 further including:

means for supplying information to said photon detecting means corresponding to the pulses of photons produced by said photon pulse producing means.

3. The system according to claim 1 wherein said photon pulse producing means includes a shutter means for periodically interposing a photon-occluding shield between said radionuclide storing means and said photon detecting means.

4. The system according to claim 3 further including:

means for supplying information to said photon detecting means corresponding to the position of said photon-occluding shield relative to said radionuclide storage means.

5. The system according to claim 1 wherein said armature means further includes:

means for adjusting the relative distance between said flood source means and said photon detecting means.

6. The system according to claim 1 further including:

means for collimating photons; and means for attaching said collimating means to said photon detecting means.

7. The system according to claim 1 wherein the radionuclide administered to said patient and the radionuclide within said radionuclide storage means are identical.

8. The system according to claim 1 wherein said emission data obtaining means and said transmission image data obtaining means obtain their respective data substantially simultaneously, without moving said patient.

9. The system according to claim 1 further including:

means for obtaining flood image data corresponding to the photons within at least one of the pulses of photons, said pulse photons being emitted by the radionuclide within said storing means, said flood data being obtained without said patient being present.

10. The system according to claim 9 further including:

means for determining attenuation coefficients from at least said transmission image data and said flood image data; and means for correcting said emission image data using said attenuation coefficients.

11. A nuclear medical imaging system comprising:

a first source means for emitting radiation from a first source of photons within a patient to thereby produce emission data;

a second source means for transmitting radiation from a second source of photons to thereby produce transmission data;

means for detecting said emission data from said first source of photons and for detecting said transmission data from said second source of photons; and means for producing image data for fiducial alignment from at least said transmission data whereby anatomical detail of the transmission data relates to the physiological aspects of the emission data.

12. The imaging system of claim 11, further comprising armature means for positioning said second source means substantially opposite said means for detecting, wherein said means for detecting detects the photons produced by said photon pulse producing means.

13. The system according to claim 11 wherein said second source means includes a shutter means for periodically interposing a photon-occluding shield between said radiation and said photon detecting means.

14. The system according to claim 11 wherein said armature means further includes:

means for adjusting the relative distance between said second source means and said means for detecting.

15. The system according to claim 11 further including:

means for collimating photons; and means for attaching said collimating means to said means for detecting.

16. A method of nuclear medical imaging comprising:

emitting radiation from a first source of photons within a patient to thereby produce emission data;

transmitting radiation from a second source of photons to thereby produce transmission data;

simultaneously detecting said emission data from said first source of photons and said transmission data from said second source of photons; and producing image data for fiducial alignment of at least the transmission data, whereby the anatomical detail of the transmission data relates to the physiological aspects of the emission data.

* * * * *